United States Patent
Shin et al.

(10) Patent No.: US 11,571,410 B2
(45) Date of Patent: Feb. 7, 2023

(54) USE OF CARBAMATE COMPOUNDS FOR PREVENTION, ALLEVIATION OR TREATMENT OF BIPOLAR DISORDER

(71) Applicant: SK BIOPHARMACEUTICALS CO., LTD., Gyeonggi-do (KR)

(72) Inventors: Yu Jin Shin, Gyeonggi-do (KR); Sei Myoung Han, Seoul (KR)

(73) Assignee: SK BIOPHARMACEUTICALS CO., LTD., Gyeonggi-do (KR)

( * ) Notice: Subject to any disclaimer, the term of this patent is extended or adjusted under 35 U.S.C. 154(b) by 90 days.

(21) Appl. No.: 16/468,782

(22) PCT Filed: Dec. 14, 2017

(86) PCT No.: PCT/KR2017/014740
§ 371 (c)(1),
(2) Date: Jun. 12, 2019

(87) PCT Pub. No.: WO2018/111008
PCT Pub. Date: Jun. 21, 2018

(65) Prior Publication Data
US 2019/0314337 A1    Oct. 17, 2019

(30) Foreign Application Priority Data
Dec. 14, 2016 (KR) .......................... 10-2016-0170224

(51) Int. Cl.
*A61K 31/41* (2006.01)
*A61P 25/18* (2006.01)

(52) U.S. Cl.
CPC .............. *A61K 31/41* (2013.01); *A61P 25/18* (2018.01)

(58) Field of Classification Search
CPC ........ A61K 31/41; A61K 31/325; A61P 25/18
See application file for complete search history.

(56) References Cited

U.S. PATENT DOCUMENTS

| | | | |
|---|---|---|---|
| 2002/0193433 A1 | 12/2002 | Plata-Salaman et al. | |
| 2012/0004300 A1* | 1/2012 | Lee | A61P 25/18 514/489 |
| 2014/0073018 A1 | 3/2014 | Lim | |

FOREIGN PATENT DOCUMENTS

| | | |
|---|---|---|
| EP | 2590645 A2 | 5/2013 |
| KR | 10-2001-0022877 A | 3/2001 |
| KR | 10-2003-0087010 A | 11/2003 |
| KR | 10-2008-0005437 A | 1/2008 |
| WO | WO-02/067921 A1 | 9/2002 |
| WO | WO-02/067924 A1 | 9/2002 |
| WO | WO-2006055603 A2 | 5/2006 |

(Continued)

OTHER PUBLICATIONS

Dencker, Antimanic efficacy of retigabine in a proposed mouse model of bipolar disorder, Behavioural Brain Research, 2010, 207, pp. 78-83. (Year: 2010).*

(Continued)

*Primary Examiner* — Savitha M Rao
*Assistant Examiner* — Andrew P Lee
(74) *Attorney, Agent, or Firm* — Harness, Dickey & Pierce, P.L.C.

(57) ABSTRACT

The present invention relates to a use for the purpose of preventing, alleviating, or treating bipolar disorder by administering a pharmaceutical composition comprising a carbamate compound of the following chemical formula 1.

6 Claims, 2 Drawing Sheets

(56) References Cited

FOREIGN PATENT DOCUMENTS

| WO | WO-2006/112685 A1 | 10/2006 |
|----|-------------------|---------|
| WO | WO-2008/054984 A1 | 5/2008 |
| WO | WO-2012/002687 A2 | 1/2012 |
| WO | WO-2016-025917 A1 | 2/2016 |

OTHER PUBLICATIONS

Diagnostic and Statistical Manual of Mental Disorders. 4th ed. Washington DC: American Psychiatric Association (2000).
Poitou P, Boulu R, Bohuon C, Effect of lithium and other drugs on the amphetamine chlordiazepoxide hyperactivity in mice. Experientia (1975) 31:99-101.
Arban R, Maraia G, Brackenborough K, Winyard L, Wilson A, Gerrard P, Large C. Evaluation of the effects of lamotrigine, valproate and carbamazepine in a rodent model of mania. Behav Brain Res (2005) 158:123-132 .
Ketter TA, Miller S, Dell'Osso B, Wang PW. Treatment of bipolar disorder: Review of evidence regarding guetiapine and lithium. J. of Affect. Disord. (2016)191:256-273.
Pacchiarotti, D.J. Bond, R.J. Baldessarini et al. The International Society for Bipolar Disorders (ISBD) task force report on antidepressant use in bipolar disorders. Am. J. Psychiatry (2013) 170:1249-1262.
Vieta E, Rosa AR. Evolving trends in the long-term treatment of bipolar disorder. World J Biol Psychiatry.(2007) 8:4-11.
International Search Report from corresponding PCT Application No. PCT/KR2017/014740, dated Mar. 21, 2018.
Extended European Search Report from corresponding European Patent Application No. 17881161.8, dated May 18, 2020.
Examination Report from corresponding Indian Patent Application No. 201947027411, dated Feb. 4, 2021.
Otsuka Pharmaceutical Co., Ltd., "Antipsychotic Agent ABILIFY® Receives Regulatory Approvals for Additional Indication "Improvement of Manic Symptoms Associated with Bipolar Disorder" and for New Dosage Form Abilify® OD Tablets" Published Jan. 18, 2012.
Modern Medical Encyclopedia, St. Petersburg, publishing house "NORINT", 2004, pp. 333-335.
Small Medical Encyclopedia, edited by Pokrovsky V.I., Moscow, Publishing house "Great Russian Encyclopedia", 1992, vol. 3, pp. 100-103.
G S Sachs et al. «The Expert Consensus Guideline Series: Medication Treatment of Bipolar Disorder 2000», A Postgraduate Medicine Special Report, 2000, pp. 1-104.
N.V. Sturov, 0 . L. Romanova "Bipolar disorders: clinical picture and principles of therapy", Difficult Patient, 2008, N4, vol. 6, pp. 49-54.

\* cited by examiner

(p<0.001), T-test, Normal mouse control group vs. Bipolar mania-induced mouse control group

(p<0.01, 10 po), * (p<0.001, 20 po), ANOVA, Bipolar mania-induced mouse control group vs. Test compound administration group Bar = SEM

USE OF CARBAMATE COMPOUNDS FOR PREVENTION, ALLEVIATION OR TREATMENT OF BIPOLAR DISORDER

CROSS-REFERENCE TO RELATED APPLICATIONS

This application is a national phase application of PCT Application No. PCT/KR2017/014740, filed on 14 Dec. 2017, which claims the benefit and priority to Korean Patent Application No. 10-2016-0170224, filed on 14 Dec. 2016. The entire disclosures of the applications identified in this paragraph are incorporated herein by references.

FIELD

The present invention relates to use of a carbamate compound of the following Formula 1 for the purpose of preventing, alleviating or treating bipolar disorder by administering a pharmaceutical composition comprising said carbamate compound:

[Formula 1]

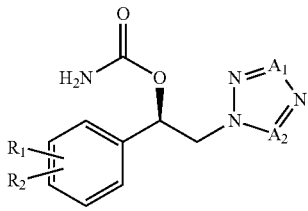

wherein,
$R_1$, $R_2$, $A_1$ and $A_2$ are as defined herein.

BACKGROUND

Bipolar disorder (BPD) is a mood disorder that is accompanied by mania and depression, which is a chronic, cyclic psychiatric disorder. According to DSM-IV, bipolar disorder is classified as bipolar disorder Type I, bipolar disorder Type II, cyclothymic disorder, and bipolar disorder not otherwise classified. When a patient has experienced more than one manic episode or a mixed episode in which depressive episodes and manic episodes occur simultaneously, he/she is diagnosed as bipolar disorder Type I. Bipolar disorder Type II refers to a case in which a patient having a medical history of at least one major depressive episode has further experienced at least one hypomanic episode (American Psychiatric Association, 2000).

Mania is characterized by at least one of the following symptoms lasting for a week: irritability, euphoria, decreased need for sleep, grandiose ideas, impulsive behavior, increased talkativeness, racing thoughts, increased activity, distractibility, etc. Mania is a condition wherein these symptoms cause severe disruption to life to such a degree that hospitalization is required. Hypomania refers to a condition in which the symptoms are similar to those of mania but the duration is shorter than that of mania and the functional change is mild so that hospitalization is not required. During depressive episodes, the patient experiences loss of attention, lack of worth, guilt, feelings of helplessness (lethargy), loss of interest, fatigue, sleeplessness or excessive sleep, weight gain or loss, suicidal impulse or attempt, etc. According to the National Comorbidity Survey Replication, the lifetime prevalence of bipolar disorder is estimated to be about 4%, and bipolar disorder has a high morbidity rate with attention deficit hyperactivity disorder (ADHD), generalized anxiety disorder, alcoholism, drug abuse and the like.

To date, the pathophysiology and causes of bipolar disorder have not been clearly elucidated. It is understood that genetic factors, biological factors, psychosocial factors, etc. work in combination and cause the onset of bipolar disorder. It is known that bipolar disorder is associated imbalance of neurotransmitters, especially dopamine, serotonin and norepinephrine, and the sensitivity of each receptor rather than the absolute amount influences the effect of a drug (i.e., alleviation of symptoms).

The aim of the treatment of bipolar disorder is to treat symptoms such as mania, hypomania and depression, and to maintain the therapeutic effect by reducing or preventing the cyclothymic properties of the disease. Lithium and antipsychotics are used as manic therapies, and benzodiazepines are considered as adjunctive therapies. Recently, many articles have raised questions about the efficacy and therapeutic superiority of lithium, but it is still considered the standard treatment for bipolar mania (Ketter et al., 2016). Early onset of lithium therapy can lead to headaches, hand shaking, weight gain, etc., and sudden cessation of therapy can lead to mania, so it is important to maintain adequate blood concentration. Second-generation antipsychotics, such as olanzapine, quetiapine, risperidone and clozapine, are likely to treat bipolar mania, but side effects such as sedation, weight gain and metabolic disorders are common (Vieta & Rosa, 2007). Antidepressants are effective for unipolar depression, but the advantages of using antidepressants in combination with mood stabilizers in bipolar depression remain controversial. Due to concerns about symptomatic switch to mania or hypomania, recent guidelines have restricted or prohibited the use of antidepressants for the treatment of bipolar depression (Pacchiarotti et al., 2013).

A variety of drugs have been used for the treatment or prevention of bipolar disorder, but there are still limitations in their use due to an unsatisfactory level of drug response or side effects. Thus, there is a need for new drugs for bipolar disorder with improved efficacy and fewer side effects.

REFERENCE DOCUMENTS

Diagnostic and Statistical Manual of Mental Disorders. 4th ed. Washington D.C.: American Psychiatric Association (2000)

Poitou P, Boulu R, Bohuon C, Effect of lithium and other drugs on the amphetamine chlordiazepoxide hyperactivity in mice. Experientia (1975) 31:99-101

Arban R, Maraia G, Brackenborough K, Winyard L, Wilson A, Gerrard P, Large C. Evaluation of the effects of lamotrigine, valproate and carbamazepine in a rodent model of mania. Behav Brain Res (2005) 158:123-132

Ketter T A, Miller S, Dell'Osso B, Wang P W. Treatment of bipolar disorder: Review of evidence regarding quetiapine and lithium. J. of Affect. Disord. (2016) 191:256-273

Pacchiarotti, D. J. Bond, R. J. Baldessarini et al. The International Society for Bipolar Disorders (ISBD) task force report on antidepressant use in bipolar disorders. Am. J. Psychiatry (2013) 170:1249-1262

Vieta E, Rosa A R. Evolving trends in the long-term treatment of bipolar disorder. World J Biol Psychiatry. (2007) 8:4-11

SUMMARY

Problem to be Solved

The present invention is intended to provide a method for the prevention, alleviation or treatment of bipolar disorder, particularly mania of bipolar disorder (bipolar mania).

The present invention is also intended to provide the use of a carbamate compound of the following Formula 1, or a pharmaceutically acceptable salt, solvate or hydrate thereof, for the prevention, alleviation or treatment of bipolar disorder, particularly mania of bipolar disorder (bipolar mania):

[Formula 1]

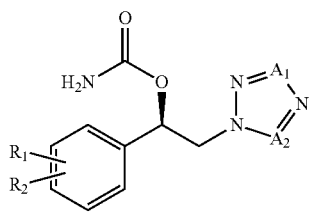

wherein,
$R_1$, $R_2$, $A_1$ and $A_2$ are as defined herein.

Technical Solution to the Problem

The present invention provides a medicament for the prevention, alleviation or treatment of bipolar disorder, particularly bipolar mania, comprising a therapeutically effective amount of a carbamate compound of the following Formula 1, or a pharmaceutically acceptable salt, solvate or hydrate thereof:

[Formula 1]

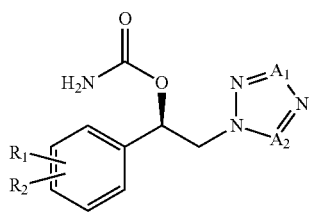

wherein,
$R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and
one of $A_1$ and $A_2$ is CH, and the other is N.

In addition, the present invention provides a pharmaceutical composition for the prevention, alleviation or treatment of bipolar disorder, particularly bipolar mania, comprising a therapeutically effective amount of the carbamate compounds of the above Formula 1, or a pharmaceutically acceptable salt, solvate or hydrate thereof, and further one or more of a pharmaceutically acceptable carrier.

In addition, the present invention provides a method for preventing, alleviating or treating bipolar disorder, particularly bipolar mania, in a subject, comprising administering to the subject a therapeutically effective amount of the carbamate compounds of the above Formula 1, or a pharmaceutically acceptable salt, solvate or hydrate thereof.

In addition, the present invention provides the use of the carbamate compounds of the above Formula 1, or a pharmaceutically acceptable salt, solvate or hydrate thereof for the prevention, alleviation or treatment of bipolar disorder, particularly bipolar mania, or for the improvement of symptoms associated therewith.

In one embodiment of the present invention, in the above Formula 1, $R_1$ and $R_2$ are each independently selected from the group consisting of hydrogen, halogen and $C_1$-$C_8$ alkyl.

In one embodiment of the present invention, the halo $C_1$-$C_8$ alkyl is perfluoroalkyl.

According to another embodiment of the present invention, the carbamate compound of the above Formula 1 is carbamic acid (R)-1-(2-chlorophenyl)-2-tetrazol-2-yl)ethyl ester of the following Formula 2:

[Formula 2]

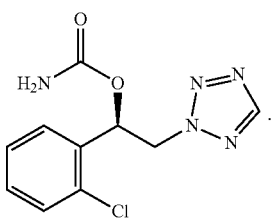

A person having ordinary skill in the art of synthesis of compounds could have easily prepared the carbamate compounds of the above Formulas 1 and 2 using known compounds or compounds which can be easily prepared therefrom. In particular, methods for preparing the compounds of the above Formula 1 are described in detail in PCT Publication Nos. WO 2006/112685 A1, WO 2010/150946 A1 and WO 2011/046380 A2, the disclosures of which are incorporated herein by reference. The compounds of the above Formula 1 can be chemically synthesized by any of the methods described in the above documents, but the methods are merely exemplary ones, and the order of the unit operation and the like may be selectively changed if necessary. Hence, the above methods are not intended to limit the scope of the invention.

The carbamate compounds of the above Formula 1 can be used for the prevention, alleviation or treatment of bipolar disorder.

Particularly, the carbamate compounds of the above Formula 1 can be used for the prevention, alleviation or treatment of mania of bipolar disorder According to one embodiment of the present invention, the bipolar disorder may be one or more selected from the group consisting of bipolar disorder Type I, bipolar disorder Type II, cyclothymic disorder and bipolar disorder not otherwise classified. More specifically, the bipolar disorder may be bipolar disorder Type I or bipolar disorder Type II.

Mania includes a hypomanic, manic or manic mood phase, regardless of the cause. Bipolar mania refers to mania associated with bipolar disorder.

In one embodiment, to confirm the efficacy on bipolar disorder, particularly on mania of bipolar disorder, the effect of the compounds of the above Formula 1 can be tested using an Amphetamine-induced hyperactivity model. The administration of Amphetamine, a central nervous system stimulant that increases dopamine neurotransmission, alone or in combination with Chlordiazepoxide, to rodents, can induce manic-like symptoms such as hyperactivity, which results in an increase in behavior in the open field test (Poitou et al., 1975; Arban et al., 2005).

The dosage of the carbamate compounds of Formula 1 for the prevention, alleviation or treatment of the above diseases may typically vary depending on the severity of the disease, the body weight and the metabolic status of the subject. A "therapeutically effective amount" for an individual patient refers to an amount of the active compound sufficient to achieve the above pharmacological effect, i.e., the therapeutic effect as described above. The therapeutically effective amount of the compounds of the present invention is 50 to 500 mg, 50 to 400 mg, 50 to 300 mg, 100 to 400 mg, 100 to 300 mg, 50 to 200 mg, or 100 to 200 mg, based on the free form and once-daily administration to humans. The therapeutically effective amount is preferably 50 to 300 mg, more preferably 50 to 200 mg.

The compounds of the present invention may be administered by any conventional method used for administration of a therapeutic agent, such as oral, parenteral, intravenous, intramuscular, subcutaneous or rectal administration.

The medicament or pharmaceutical composition according to one embodiment of the present invention may comprise a therapeutically effective amount of a compound selected from the group consisting of the carbamate compounds of the present invention, their pharmaceutically acceptable salts, solvates, hydrates and combinations thereof.

Examples of the pharmaceutically acceptable salts of the carbamate compounds of the above Formula 1 include independently, acetate, benzenesulfonate, benzoate, bitartrate, calcium acetate, camsylate, carbonate, citrate, edetate, edisylate, estolate, esylate, fumarate, gluceptate, gluconate, glutamate, glycoloyl arsanilate, hexylresorcinate, hydravamine, hydrobromide, hydrochloride, hydrogencarbonate, hydroxynaphthoate, iodide, isethionate, lactate, lactobionate, malate, maleate, mandelate, mesylate, methylnitrate, methylsulfate, mucate, napsylate, nitrate, pamoate (embonate), pantothenate, phosphate/diphosphate, polygalacturonate, salicylate, stearate, subacetate, succinate or hemisuccinate, sulfate or hemi-sulfate, tannate, tartrate, oxalate or hemi-tartrate, teoclate, triethiodide, benzathine, chloroprocaine, choline, diethanolamine, ethylenediamine, meglumine, procaine, aluminum, ammonium, tetramethylammonium, calcium, lithium, magnesium, potassium, sodium and zinc.

The medicament or pharmaceutical composition according to one embodiment of the present invention may be administered orally or parenterally. The parenteral administration may include intravenous injection, subcutaneous injection, intramuscular injection, intraperitoneal injection, endothelial administration, topical administration, intranasal administration, intravaginal administration, intrapulmonary administration, rectal administration and the like. In the case of oral administration, the pharmaceutical composition according to one embodiment of the present invention may be formulated as a plain tablet (uncoated tablet) or such that the active agent is coated or it is protected against degradation in the stomach. In addition, the composition can be administered by any device capable of transferring the active substance to a target cell. The route of administration may vary depending upon the general condition and age of the subject to be treated, the nature of the treatment condition and the active ingredient selected.

A suitable dosage of the medicament or pharmaceutical composition according to one embodiment of the present invention may vary depending on factors such as the formulation method, administration method, age, body weight and gender of patients, pathological condition, diet, administration time, administration route, excretion rate and reaction sensitivity, and doctors having ordinary skill can easily determine and prescribe dosages that are effective for the desired treatment or prophylaxis. The pharmaceutical composition according to one embodiment may be administered in one or more doses, for example, one to four times per day. The pharmaceutical composition according to one embodiment may contain the compounds of Formula 1 in the amount of 50 to 500 mg, 50 to 400 mg, 50 to 300 mg, 100 to 400 mg, 100 to 300 mg, 50 to 200 mg, or 100 to 200 mg, preferably 50 to 300 mg, more preferably 50 to 200 mg, based on the free form.

The medicament or pharmaceutical composition according to one embodiment of the present invention may be formulated using a pharmaceutically acceptable carrier and/or excipient according to a method that a person having ordinary skill in the art could easily carry out, thereby to be prepared in a unit dose form or to be contained in a multi-dose container. The above formulation may be a solution in oil or an aqueous medium, a suspension or an emulsion (emulsified solution), an extract, a powder, granules, a tablet, or a capsule, and may further include a dispersing or stabilizing agent. In addition, the pharmaceutical composition may be administered in the form of suppositories, sprays, ointments, creams, gels, inhalants or skin patches. The pharmaceutical composition may also be prepared for mammalian administration, more preferably for human administration.

Pharmaceutically acceptable carriers may be solid or liquid, and may be one or more selected from fillers, antioxidants, buffers, bacteriostats, dispersants, adsorbents, surfactants, binders, preservatives, disintegrants, sweeteners, flavors, glidants, release-controlling agents, wetting agents, stabilizers, suspending agents, and lubricants. In addition, the pharmaceutically acceptable carriers may be selected from saline, sterile water, Ringer's solution, buffered saline, dextrose solution, maltodextrin solution, glycerol, ethanol and mixtures thereof.

In one embodiment, suitable fillers include, but are not limited to, sugar (e.g., dextrose, sucrose, maltose and lactose), starch (e.g., corn starch), sugar alcohol (e.g., mannitol, sorbitol, maltitol, erythritol and xylitol), starch hydrolysate (e.g., dextrin and maltodextrin), cellulose or cellulose derivatives (e.g., microcrystalline cellulose) or mixtures thereof.

In one embodiment, suitable binders include, but are not limited to, povidone, copovidone, methylcellulose, hydroxypropylmethylcellulose, hydroxypropylcellulose, hydroxyethylcellulose, gelatin, gum, sucrose, starch or mixtures thereof.

In one embodiment, suitable preservatives include, but are not limited to, benzoic acid, sodium benzoate, benzyl alcohol, butylated hydroxyanisole, butylated hydroxytoluene, chlorbutol, gallate, hydroxybenzoate, EDTA or mixtures thereof.

In one embodiment, suitable disintegrants include, but are not limited to, sodium starch glycolate, cross-linked polyvinylpyrrolidone, cross-linked carboxymethylcellulose, starch, microcrystalline cellulose or mixtures thereof.

In one embodiment, suitable sweeteners include, but are not limited to, sucralose, saccharin, sodium saccharin, potassium saccharin, calcium saccharin, acesulfame potassium or sodium cyclamate, mannitol, fructose, sucrose, maltose or mixtures thereof.

In one embodiment, suitable glidants include, but are not limited to, silica, colloidal silicon dioxide, talc and the like.

In one embodiment, suitable lubricants include, but are not limited to, long chain fatty acids and salts thereof, such as magnesium stearate and stearic acid, talc, glyceride wax or mixtures thereof.

As used herein, the terms "prevent," "preventing" and "prevention" refer to reducing or eliminating the likelihood of a disease.

As used herein, the terms "alleviate," "alleviating" and "alleviation" refer to ameliorating a disease and/or its accompanying symptoms altogether or in part.

As used herein, the terms "treat," "treating" and "treatment" refer to eliminating a disease and/or its accompanying symptoms altogether or in part.

As used herein, the term "subject" refers to an animal that is the object of therapy, observation or experiment, preferably a mammal (such as primates (e.g., a human), cattle, sheep, goats, horses, dogs, cats, rabbits, rats, mice, etc.), most preferably a human.

As used herein, the term "therapeutically effective amount" refers to the amount of active compound or pharmaceutical formulation that elicits a biological or medical response in the system, animal or human, including alleviation of the symptoms of the disease or disorder to be treated, wherein said amount is sought by a researcher, veterinarian, doctor (physician) or other clinician.

As used herein, the term "composition" encompasses a product that contains a specified amount of a particular ingredient and any product that results directly or indirectly from a combination of specified amounts of particular ingredients.

Effect of the Invention

The medicament and the pharmaceutical composition according to the present invention can effectively treat and prevent bipolar disorder, more particularly bipolar mania.

DETAILED DESCRIPTION

Figure 1:
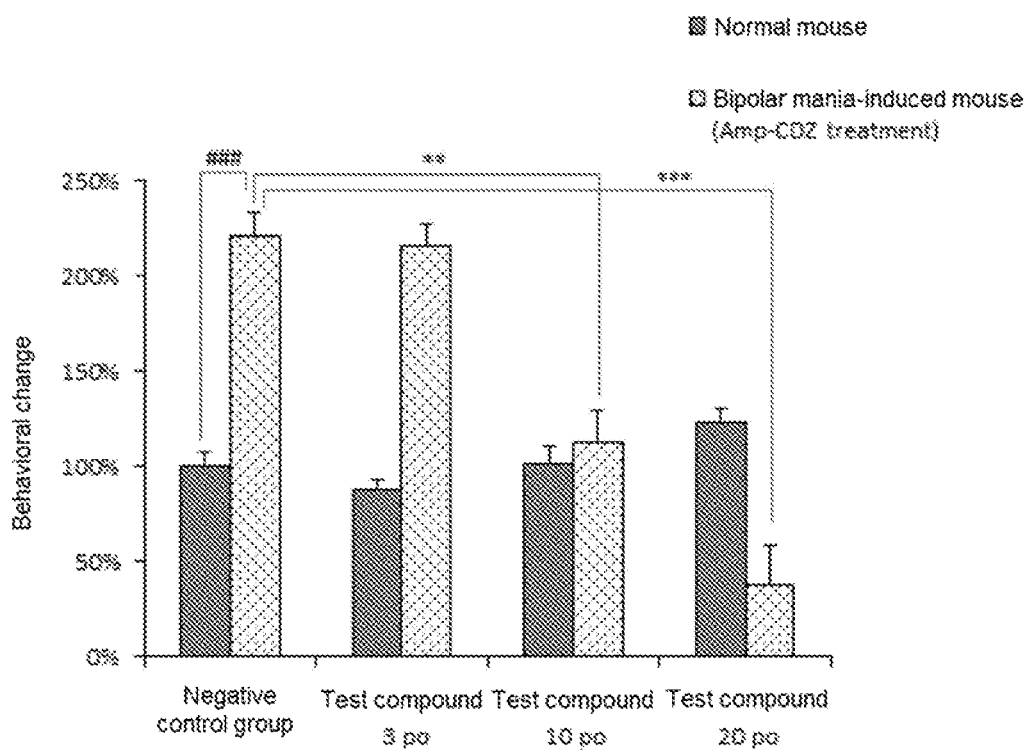
FIG. 1 shows behavioral changes compared with the vehicle-administered negative control group after administration of carbamic acid (R)-1-(2-chlorophenyl)-2-tetrazol-2-yl)ethyl ester prepared in the Preparation Example (the compound of Formula 2, hereinafter referred to as "the test compound") to normal mice and bipolar mania-induced mice.

Hereinafter, the present invention will be explained in more detail through working examples. However, the following working examples are only intended to illustrate one or more embodiments and are not intended to limit the scope of the invention.

Preparation Example: Synthesis of Carbamic Acid (R)-1-(2-chlorophenyl)-2-tetrazol-2-yl)ethyl ester Carbamic acid (R)-1-(2-chlorophenyl)-2-tetrazol-2-yl) ethyl ester was prepared according to the method described in Preparation Example 50 of PCT Publication No. WO 2010/150946.

Example: Experiment of Pharmacological Effect for Treatment of Mania in Mouse Bipolar Mania Model Male ICR mice weighing 20 to 25 g were purchased from Orient Bio and used in this experiment. Animals were stabilized for more than 4 days under conditions of standard temperature (19 to 25° C.), humidity (40 to 60%), free access to food and water, and controlled light (illuminated from 7 am to 7 pm), and then used. 158 mice were divided into the following groups. Compounds to be administered to mice in each group were prepared by dissolving them in 30% polyethylene glycol 400 (Sigma), and orally administered to mice at a volume of 10 ml/kg.

Normal Mouse Group (7 to 8 Mice Per Group)
  Mice as a negative control group, once orally administered with 30% PEG400 as a vehicle at a dose of 10 ml/kg
  Mice once orally administered with the test compound at a dose of 5, 10 and 20 mg/kg
  Mice as a positive control group, once orally administered with valproic acid at a dose of 300 mg/kg Bipolar Mania-Induced Mouse Group (10 to 14 Mice Per Group, Administered with the Combination of Amphetamine and Chlordiazepoxide after Administration of the Following Control Compound and the Test Compound)
  Mice as a negative control group, once orally administered with 30% PEG400 as a vehicle at a dose of 10 ml/kg
  Mice once orally administered with the test compound at a dose of 5, 10 and 20 mg/kg
  Mice as a positive control group, once orally administered with valproic acid at a dose of 300 mg/kg To determine the concentration of the positive control compound and the test compound, valproic acid 300 mg/kg and the test compound 5, 10 and 20 mg/kg were each orally administered to normal mice. After 1 hour, an open field test was conducted for 30 minutes using Opto-Varimax® (Columbus Instruments, Ohio, USA) equipment, and it was confirmed that the behavior in these groups did not significantly decrease compared with the vehicle-administered negative control group [FIGS. 1 and 2: normal m ice].

The combined preparation of Amphetamine 2.5 mg/kg and Chlordiazepoxide 2.5 mg/kg was intraperitoneally administered to mice to induce mania, and 30 minutes after administration the behavior was measured in the open field test for 30 minutes. Analysis of the measured behavior by one-tailed student's t test compared with the negative control group administered with only the vehicle indicated that the behavior significantly increased (p<0.05) [FIGS. 1 and 2: normal mouse control group vs. bipolar mania-induced mouse control group]. Hence, this was used as the bipolar mania induction condition (Arban et al., 2005).

In order to confirm the effect of the positive control compound and the test compound to prevent mania in mania-induced models (inhibition of increased behavior), valproic acid 300 mg/kg, and the test compound 5, 10 and 20 mg/kg were each orally administered to mice in each group. After 30 minutes, the combined preparation of Amphetamine and Chlordiazepoxide was intraperitoneally administered. 30 minutes after intraperitoneal administration, the open field test was conducted for 30 minutes. The behavioral changes in the test group compared to the negative control group (100%) was analyzed by one-way ANOVA, which confirmed the efficacy (p<0.05), and the results are shown in FIGS. 1 and 2.

Figure 2:
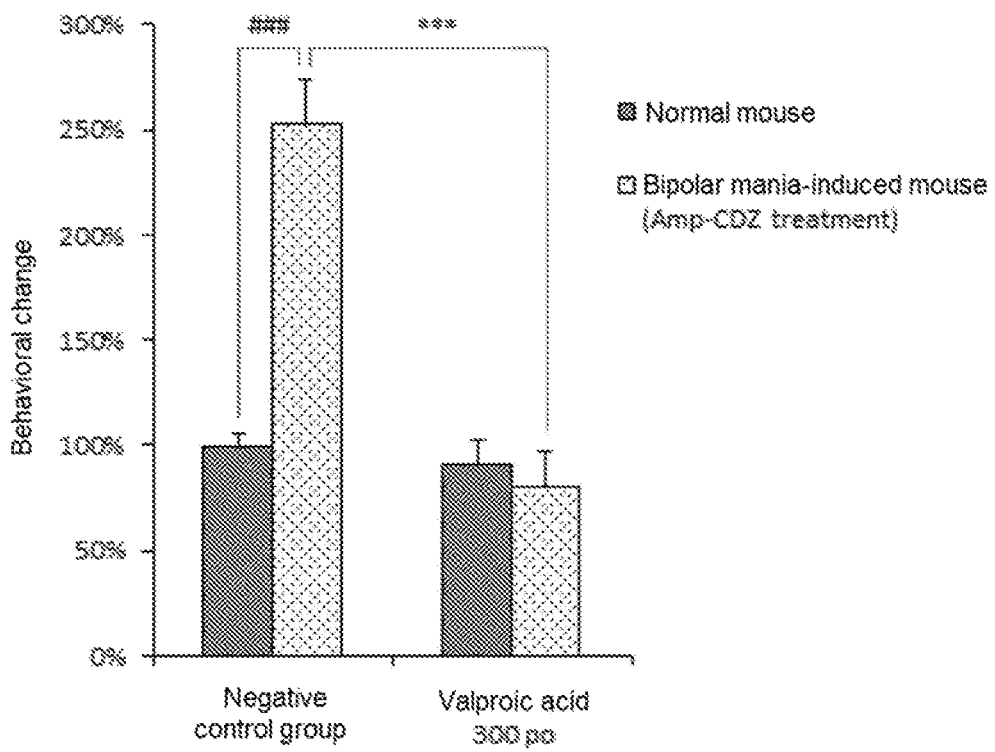
FIG. 2 shows behavioral changes compared with the vehicle-administered negative control group after administration of the positive control compound valproic acid to normal mice and bipolar mania-induced mice.

Administration of the test compound in the mania-induced mice reduced the behavior in the open field test versus the vehicle-treated group (negative control group) (FIG. 1), and especially at doses of 10 mg/kg or more of the test compound the efficacy was similar or better than that of valproic acid at 300 mg/kg (FIG. 2). The test compound did not affect the behavior of the normal mice up to doses of 20 mg/kg, whereas it significantly reduced mania in the mania-induced mice, indicating that the test compound can treat bipolar mania without affecting normal behavior (FIG. 1).

From the above results, it was confirmed that the present compounds showed sufficient pharmacological effect to inhibit an increase in behavior in the bipolar mania models and no effect on behavior of normal mice, and thus the present compounds can be effectively used as a drug for treating bipolar mania.

What is claimed is:

1. A method for alleviating or treating mania in a subject suffering from bipolar disorder, comprising administering to the subject a therapeutically effective amount of a carbamate compound of the following Formula 1, or a pharmaceutically acceptable salt, solvate or hydrate thereof:

[Formula 1]

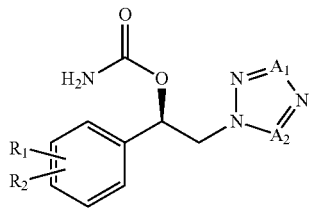

wherein, $R_1$ and $R_2$ are each independently selected from the group consisting of hydrogen, halogen, $C_1$-$C_8$ alkyl, halo-$C_1$-$C_8$ alkyl, $C_1$-$C_8$ thioalkoxy and $C_1$-$C_8$ alkoxy; and one of $A_1$ and $A_2$ is CH, and the other is N.

2. The method according to claim 1, wherein $R_1$ and $R_2$ are each independently selected from the group consisting of hydrogen, halogen and $C_1$-$C_8$ alkyl.

3. The method according to claim 1, wherein the carbamate compound of Formula 1 is carbamic acid (R)-1-(2-chlorophenyl)-(2-tetrazol-2-yl)ethyl ester of the following Formula 2:

[Formula 2]

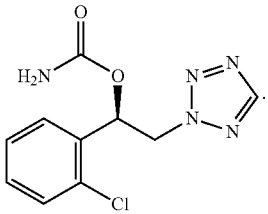

4. The method according to claim 1, wherein the subject is a mammal.

5. The method according to claim 4, wherein the mammal is a human.

6. The method according to claim 1, wherein the therapeutically effective amount of the carbamate compound of Formula 1 is 50 mg to 500 mg based on the free form.

* * * * *